(12) United States Patent
Iwama et al.

(10) Patent No.: US 10,866,233 B2
(45) Date of Patent: Dec. 15, 2020

(54) ANALYSIS DEVICE AND ANALYSIS METHOD

(71) Applicant: JVC KENWOOD Corporation, Yokohama (JP)

(72) Inventors: Shigehiko Iwama, Yokohama (JP); Makoto Itonaga, Yokohama (JP); Yuichi Hasegawa, Yokohama (JP); Koji Tsujita, Yokohama (JP); Masayuki Ono, Yokohama (JP)

(73) Assignee: JVC KENWOOD CORPORATION, Yokohama (JP)

( * ) Notice: Subject to any disclaimer, the term of this patent is extended or adjusted under 35 U.S.C. 154(b) by 35 days.

(21) Appl. No.: 16/034,734

(22) Filed: Jul. 13, 2018

(65) Prior Publication Data

US 2018/0321227 A1 Nov. 8, 2018

Related U.S. Application Data

(63) Continuation of application No. PCT/JP2016/087485, filed on Dec. 16, 2016.

(30) Foreign Application Priority Data

Feb. 3, 2016 (JP) .................................. 2016-018977

(51) Int. Cl.
    *G01N 33/53* (2006.01)
    *G01N 33/543* (2006.01)
    *G01N 21/55* (2014.01)

(52) U.S. Cl.
    CPC ......... *G01N 33/5302* (2013.01); *G01N 21/55* (2013.01); *G01N 33/53* (2013.01); *G01N 33/54346* (2013.01); *G01N 33/54366* (2013.01)

(58) Field of Classification Search
    None
    See application file for complete search history.

(56) References Cited

U.S. PATENT DOCUMENTS

| 6,327,031 | B1* | 12/2001 | Gordon | G01N 21/253 356/436 |
| 6,623,696 | B1* | 9/2003 | Kim | B01J 19/0046 422/401 |
| 7,157,049 | B2* | 1/2007 | Valencia | G01N 15/1475 422/50 |
| 2003/0156763 | A1* | 8/2003 | Soderman | G01N 21/6402 382/262 |
| 2004/0181343 | A1* | 9/2004 | Wigstrom | B01L 3/502715 702/19 |
| 2006/0223169 | A1* | 10/2006 | Bedingham | G01N 21/645 435/287.2 |
| 2007/0095393 | A1* | 5/2007 | Zucchelli | F16K 99/0001 137/68.11 |
| 2008/0142730 | A1* | 6/2008 | Makiuchi | G01N 21/645 250/458.1 |
| 2015/0044096 | A1* | 2/2015 | Nakasawa | G01N 35/04 422/64 |
| 2019/0293640 | A1* | 9/2019 | Iwama | G01N 33/54353 |

FOREIGN PATENT DOCUMENTS

| JP | 572113 A | 3/1993 |
| JP | 200963310 A | 3/2009 |
| JP | 2015127691 A | 7/2015 |
| WO | WO 03036337 | * 10/2002 |
| WO | 03/036337 A2 | 5/2003 |

OTHER PUBLICATIONS

European Search Report No. 16889427.7-1111 dated Oct. 25, 2018 corresponding to Japanese PCT 2016087485.

* cited by examiner

*Primary Examiner* — Ann Y Lam
(74) *Attorney, Agent, or Firm* — Nath, Goldberg & Meyer; Jerald L. Meyer

(57) ABSTRACT

An analysis device includes a turntable, an optical pickup, and a controller. The turntable holds a specimen analysis disc having reaction regions on which nanoparticles binding to substances to be detected are captured. The optical pickup emits laser light to each reaction region, receives a reflected light from each reaction region, and generates a light reception level signal. The controller sequentially generates a plurality of measurement gate signals for counting the number of the nanoparticles captured on each reaction region, counts the number of the nanoparticles of each of the measurement gate signals based on the light reception level signal, specifies a measurement gate section in each reaction region according to a measurement result per measurement gate signal, and adds up the number of the nanoparticles of the respective measurement gate signals in the measurement gate section.

4 Claims, 13 Drawing Sheets

ANALYSIS DEVICE AND ANALYSIS METHOD

CROSS REFERENCE TO RELATED APPLICATION

This application is a Continuation of PCT Application No. PCT/JP2016/087485, filed on Dec. 16, 2016, and claims the priority of Japanese Patent Application No. 2016-018977, filed on Feb. 3, 2016, the entire contents of both of which are incorporated herein by reference.

BACKGROUND

The present disclosure relates to an analysis device and an analysis method for analyzing biomaterials such as antigens and antibodies.

Immunoassays are known to quantitatively analyze disease detection and therapeutic effects by detecting particular antigens or antibodies as biomarkers associated with diseases.

Japanese Unexamined Patent Application Publication No. 2015-127691 (Patent Literature 1) discloses an analysis device in which antibodies that are fixed to a reaction region on a specimen analysis disc are allowed to bind to antigens in a specimen, and the antigens are labeled by nanoparticles having antibodies and then are scanned with laser light emitted from an optical pickup so as to detect the nanoparticles captured on the reaction region. The analysis device disclosed in Patent Literature 1 is an optical disc device utilized for detecting a specimen.

SUMMARY

In the conventional analysis device as disclosed in Patent Literature 1, a cartridge is attached to the specimen analysis disc to form wells. A sample solution and a buffer solution are injected into the wells so that an antigen-antibody reaction is promoted therein to form reaction regions. The wells thus function as holders for storing the sample solution and the buffer solution. A gasket formed of elastically-deformable material such as silicone rubber is placed between the specimen analysis disc and the cartridge, so as to decrease leakage of the solutions.

Since the gasket is elastically deformable, the cartridge may be fixed to the specimen analysis disc via the gasket in the deformed state. A tolerance of positioning between the cartridge and the specimen analysis disc or displacement of the cartridge on the specimen analysis disc caused by the deformation of the gasket may shift the reaction regions from predetermined positions on the specimen analysis disc.

If the reaction regions are displaced from the predetermined positions, a timing of measurement gate signals which turn to an ON state only during a period of detecting the nanoparticles in each reaction region does not conform to a timing of nanoparticle pulse signals actually detected in each reaction region. Such inconformity leads to a decrease in accuracy of detection of the nanoparticles.

A first aspect of one or more embodiments provide an analysis device including: a turntable holding a specimen analysis disc having a reaction region on which nanoparticles binding to substances to be detected are captured; a turntable drive unit configured to rotate the turntable; a turntable drive circuit configured to control the turntable drive unit; an optical pickup driven in a direction perpendicular to a rotation axis of the turntable, and configured to emit laser light to the reaction region, to receive a reflected light from the reaction region, and to generate a light reception level signal; an optical pickup drive circuit configured to control an operation of the optical pickup; and a controller configured to control the turntable drive circuit and the optical pickup drive circuit, wherein the controller sequentially generates a plurality of measurement gate signals for counting a number of the nanoparticles captured on the reaction region, counts the number of the nanoparticles of each of the measurement gate signals based on the light reception level signal, specifies a measurement gate section in the reaction region according to a measurement result per measurement gate signal, and adds up the number of the nanoparticles of the respective measurement gate signals in the measurement gate section.

A second aspect of one or more embodiments provide an analysis method including: rotating a specimen analysis disc having a reaction region on which nanoparticles binding to substances to be detected are captured and emitting laser light to the reaction region; receiving a reflected light from the reaction region and generating a light reception level signal; sequentially generating a plurality of measurement gate signals for counting a number of the nanoparticles captured on the reaction region; counting the number of the nanoparticles of each of the measurement gate signals based on the light reception level signal; specifying a measurement gate section in the reaction region according to a measurement result per measurement gate signal; and adding up the number of the nanoparticles of the respective measurement gate signals in the measurement gate section.

DETAILED DESCRIPTION

[Detection-Target-Substance Capture Unit]

A detection-target-substance capture unit according to one or more embodiments is described below with reference to FIG. 1A, FIG. 1B, FIG. 2A, FIG. 2B, and FIG. 3.

Figure 1A:
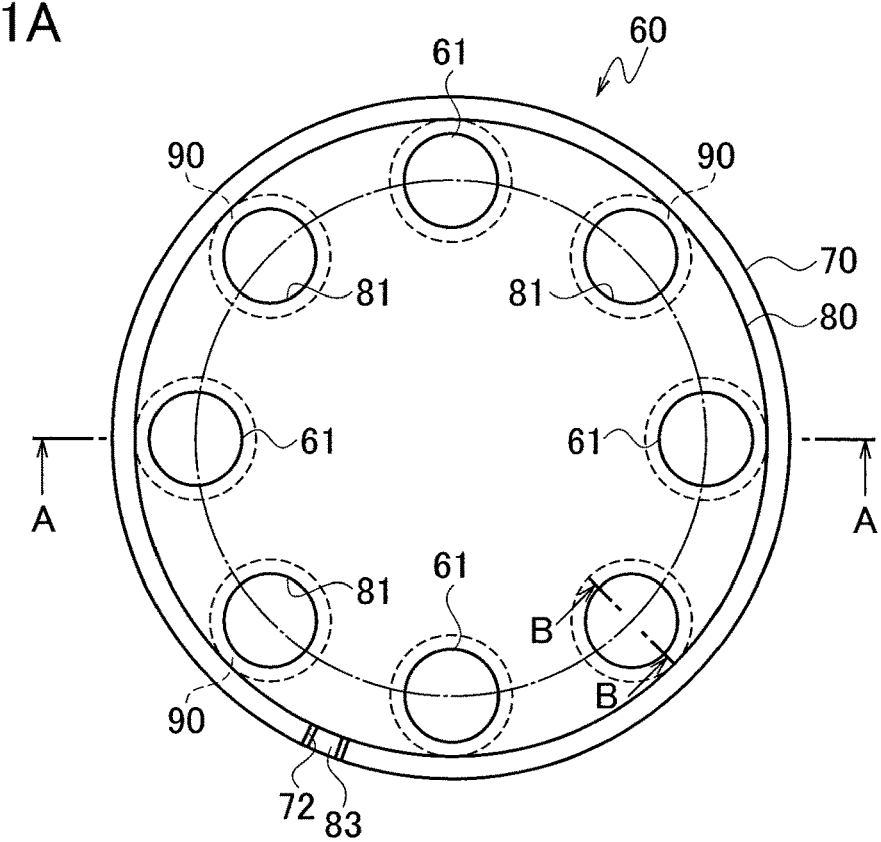
FIG. 1A is a plan view of a detection-target-substance capture unit according to one or more embodiments as viewed from a cartridge side.
Figure 1B:
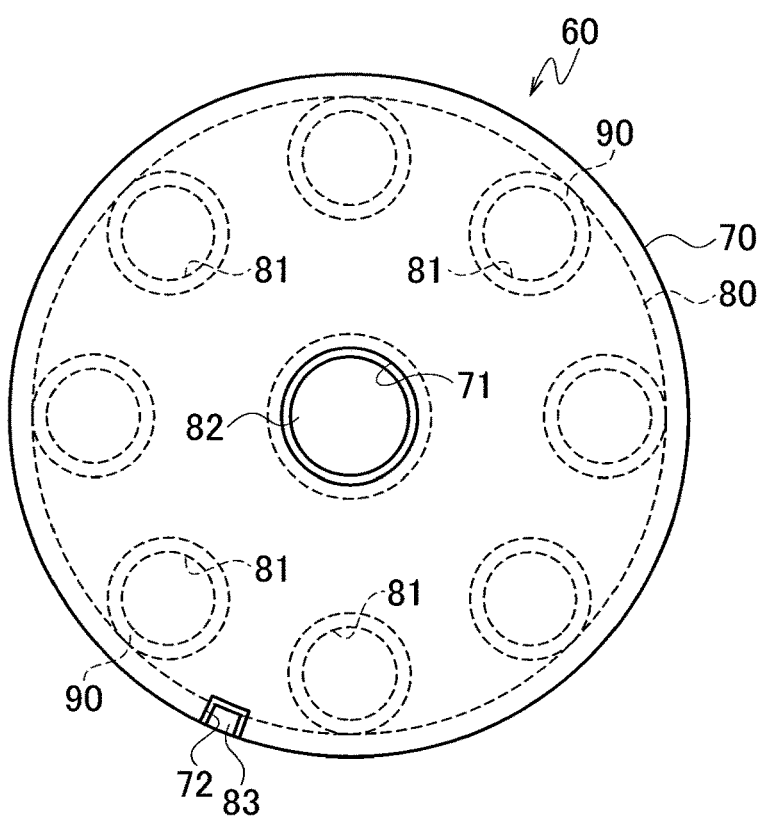
FIG. 1B is a plan view of the detection-target-substance capture unit according to one or more embodiments as viewed from a specimen analysis disc side.
Figure 2A:
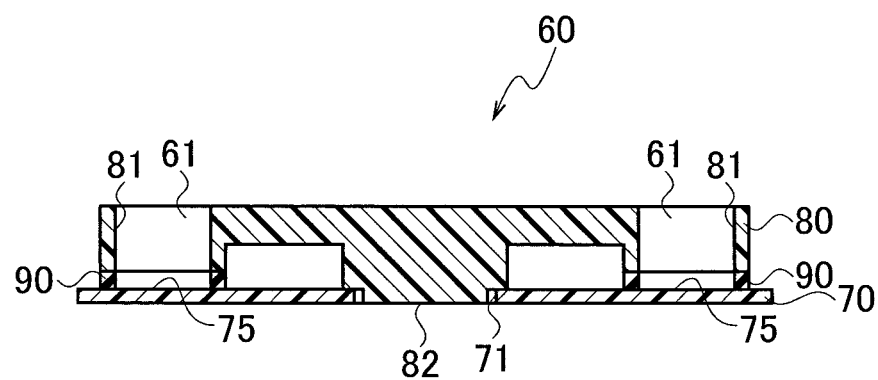
FIG. 2A is a cross-sectional view of the detection-target-substance capture unit taken along line A-A in FIG. 1A.
Figure 2B:
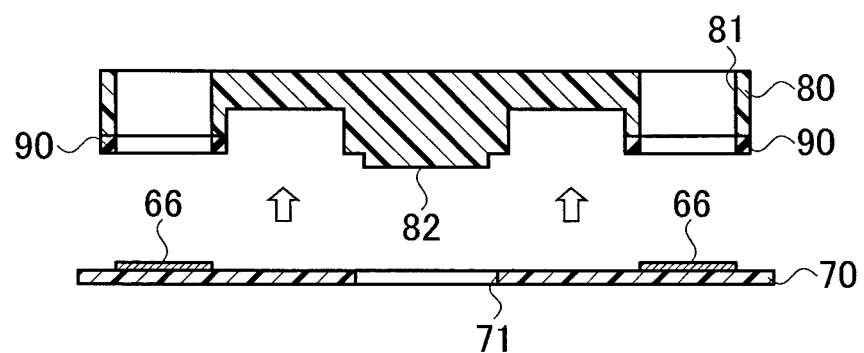
FIG. 2B is a cross-sectional view of the cartridge in FIG. 2A removed from the specimen analysis disc.
Figure 3:
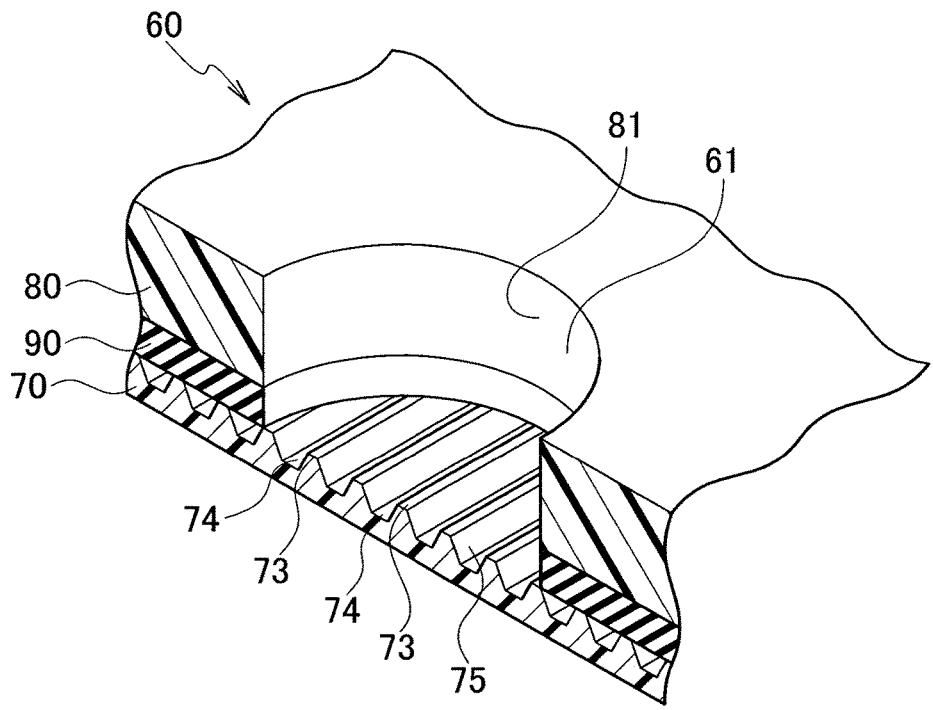
FIG. 3 is an enlarged perspective view showing a well cross-sectioned along line B-B in FIG. 1A.

FIG. 1A illustrates the detection-target-substance capture unit according to one or more embodiments as viewed from the cartridge side. FIG. 1B illustrates the detection-target-substance capture unit as viewed from the specimen analysis disc side. FIG. 2A is a cross-sectional view of the detection-target-substance capture unit taken along line A-A in FIG. 1A. FIG. 2B illustrates a state in which the cartridge is removed from the specimen analysis disc. FIG. 3 illustrates a well cross-sectioned along line B-B in FIG. 1A.

As shown in FIG. 1A and FIG. 1B, the detection-target-substance capture unit 60 includes the specimen analysis disc 70, the cartridge 80, and a seal member 90.

The specimen analysis disc 70 is formed into a circular shape having substantially the same dimensions as optical discs such as Blu-ray discs (BDs), DVDs, and compact discs (CDs). The specimen analysis disc 70 is formed of resin material such as polycarbonate resin and cycloolefin polymer, commonly used for optical discs. The specimen analysis disc 70 is not limited to the optical discs described above and may be any optical disc according to other embodiments or conforming to prescribed standards.

The specimen analysis disc 70 has a center hole 71 formed in the middle of the disc, and a slit 72 provided at the circumferential edge of the disc. The slit 72 serves as a reference position defining portion for defining a reference position of the specimen analysis disc 70.

As shown in FIG. 3, the surface of the specimen analysis disc 70 includes track regions 75 provided with convex regions 73 and recesses 74 alternately arranged in a radial direction. The convex regions 73 and the recesses 74 are formed in a spiral from the inner side to the outer side of the specimen analysis disc 70. The convex regions 73 correspond to lands of an optical disc. The recesses 74 correspond to grooves of an optical disc. A track pitch of the recesses 74 in the radial direction is 320 nm, for example.

As shown in FIG. 1A, the cartridge 80 is provided with a plurality of cylindrical penetration holes 81 arranged along the circumferential direction. The penetration holes 81 are arranged at regular intervals such that the respective center points are located on the common circle.

As shown in FIG. 1A, FIG. 1B, and FIG. 2B, the cartridge 80 includes a convex region 82 in the middle and a convex region 83 at the circumferential edge.

As shown in FIG. 1B and FIG. 2A, when the cartridge 80 is attached to the specimen analysis disc 70, the convex region 82 is inserted into the center hole 71 of the specimen analysis disc 70, and the convex region 83 is inserted into the slit 72 so that the cartridge 80 and the specimen analysis disc 70 are fitted to each other.

As shown in FIG. 2A, the seal member 90 is placed between the cartridge 80 and the specimen analysis disc 70. The seal member 90 is a ring-like gasket formed of elastically-deformable material such as silicone rubber, for example. The seal member 90 is provided along the circumference of the respective penetration holes 81. When the cartridge 80 is attached to the specimen analysis disc 70, the seal members 90 are elastically deformed to fill the recesses of the track regions 75. FIG. 3 illustrates a state before the seal member 90 is elastically deformed.

As shown in FIG. 2A and FIG. 3, the detection-target-substance capture unit 60 includes a plurality of wells 61 defined by the penetration holes 81 of the cartridge 80, the seal members 90, and the track regions 75 of the specimen analysis disc 70. The inner surfaces defined by the penetration holes 81 and the seal members 90 correspond to the inner surfaces of the wells 61, and the track regions 75 of the specimen analysis disc 70 correspond to the bottoms of the wells 61. The wells 61 each serve as a holder for storing a solution such as a sample solution and a buffer solution. The seal member 90 decreases leakage of the solution from the wells 61.

Although FIG. 1A illustrates eight wells 61, the number of wells 61 is not limited to eight.

As shown in FIG. 2B, the cartridge 80 is detachable from the specimen analysis disc 70. Nanoparticles for labeling substances to be detected are detected and measured only by use of the specimen analysis disc 70 separated from the cartridge 80.

[Formation of Reaction Region]

Figure 4:
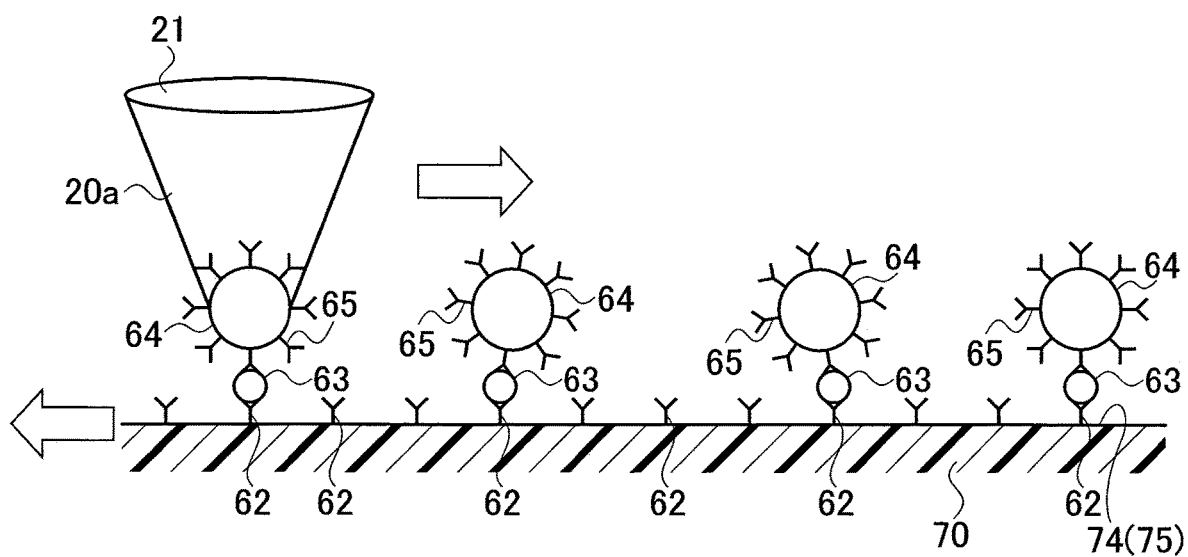
FIG. 4 is an enlarged cross-sectional view schematically illustrating a state in which substances to be detected are captured and sandwiched between antibodies and nanoparticles in a recess of a track region.
Figure 5:
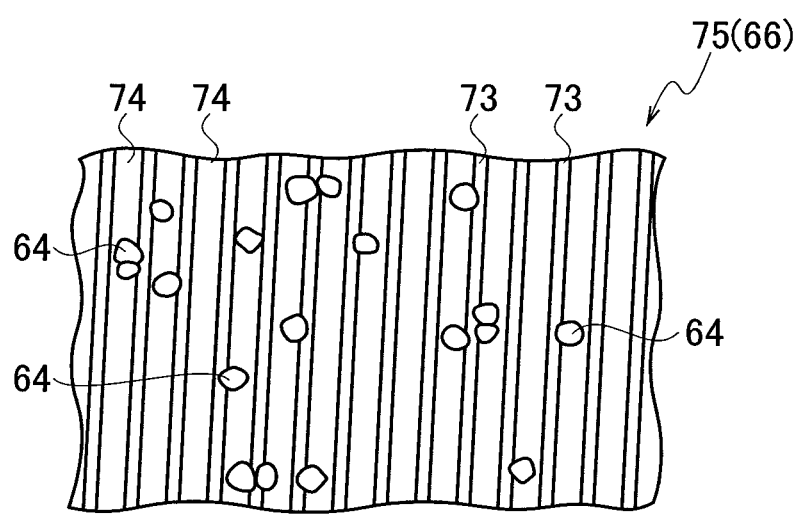
FIG. 5 is a schematic plan view illustrating a state in which the nanoparticles and the substances to be detected coupled together are captured in recesses of the track region.

An example of a method of forming the reaction regions on the specimen analysis disc 70 of the detection-target-substance capture unit 60 is described below with reference to FIG. 4 and FIG. 5.

A buffer solution including antibodies 62 is injected into the wells 61 of the detection-target-substance capture unit 60 and then incubated. The antibodies 62 are thus fixed to the track regions 75 of the specimen analysis disc 70 which are the bottoms of the wells 61, as shown in FIG. 4.

After the buffer solution is drained to clean the wells 61, a buffer solution including substances to be detected (exosomes) 63 (hereinafter, referred to as "detection target substances 63") which are antigens is injected into the wells 61 and incubated. The detection target substances 63 specifically bind to the antibodies 62 by the antigen-antibody reaction. The detection target substances 63 are thus captured on the track regions 75, more particularly, on the recesses 74 of the track regions 75. The size of the exosomes, which are the detection target substances 63, is approximately 100 nm.

After the buffer solution is drained to clean the wells 61, a buffer solution including nanoparticles 64 serving as labels is injected into the wells 61 and then incubated. Antibodies 65, which specifically bind to the detection target substances 63 by the antigen-antibody reaction, are fixed to surfaces of the nanoparticles 64. The size of the nanoparticles 64 is approximately 200 nm.

The nanoparticles 64 binding to the detection target substances 63 are captured on the recesses 74 of the track regions 75. The detection target substances 63 are captured and sandwiched between the antibodies 62 and the nanoparticles 64 on the recesses 74 of the track regions 75. FIG. 5 illustrates the state in which the nanoparticles 64 binding to the detection target substances 63 are captured on the recesses 74 of the track regions 75.

As shown in FIG. 2B, the cartridge 80 and the seal member 90 are removed from the specimen analysis disc 70. The track regions 75 corresponding to the bottoms of the wells 61 on the specimen analysis disc 70 are reaction regions 66 in which the detection target substances 63 and the nanoparticles 64 are captured by the antigen-antibody reaction. The specimen analysis disc 70 is thus provided with a plurality of reaction regions 66, corresponding to the wells 61, on which the nanoparticles 64 serving as labels are captured.

[Analysis Device]

An analysis device according to one or more embodiments is described below with reference to FIG. 6.

It is difficult to optically detect the detection target substances 63 directly, since the detection target substances 63 are exosomes having a size as small as 100 nm. The analysis device 1 according to one or more embodiments detects and counts the nanoparticles 64 captured on the reaction regions 66, so as to indirectly detect and count the detection target substances 63 specifically binding to the nanoparticles 64.

The analysis device 1 includes a turntable 2, a clamper 3, a turntable drive unit 4, a turntable drive circuit 5, a reference position detection sensor 6, a guide shaft 7, an optical pickup 20, an optical pickup drive circuit 8, a controller 9, a storage unit 10, and a display unit 11. The analysis device 1 does not necessarily include the display unit 11, and an external display unit may be used instead.

The specimen analysis disc 70 is placed on the turntable 2 with the reaction regions 66 facing down.

Figure 6:
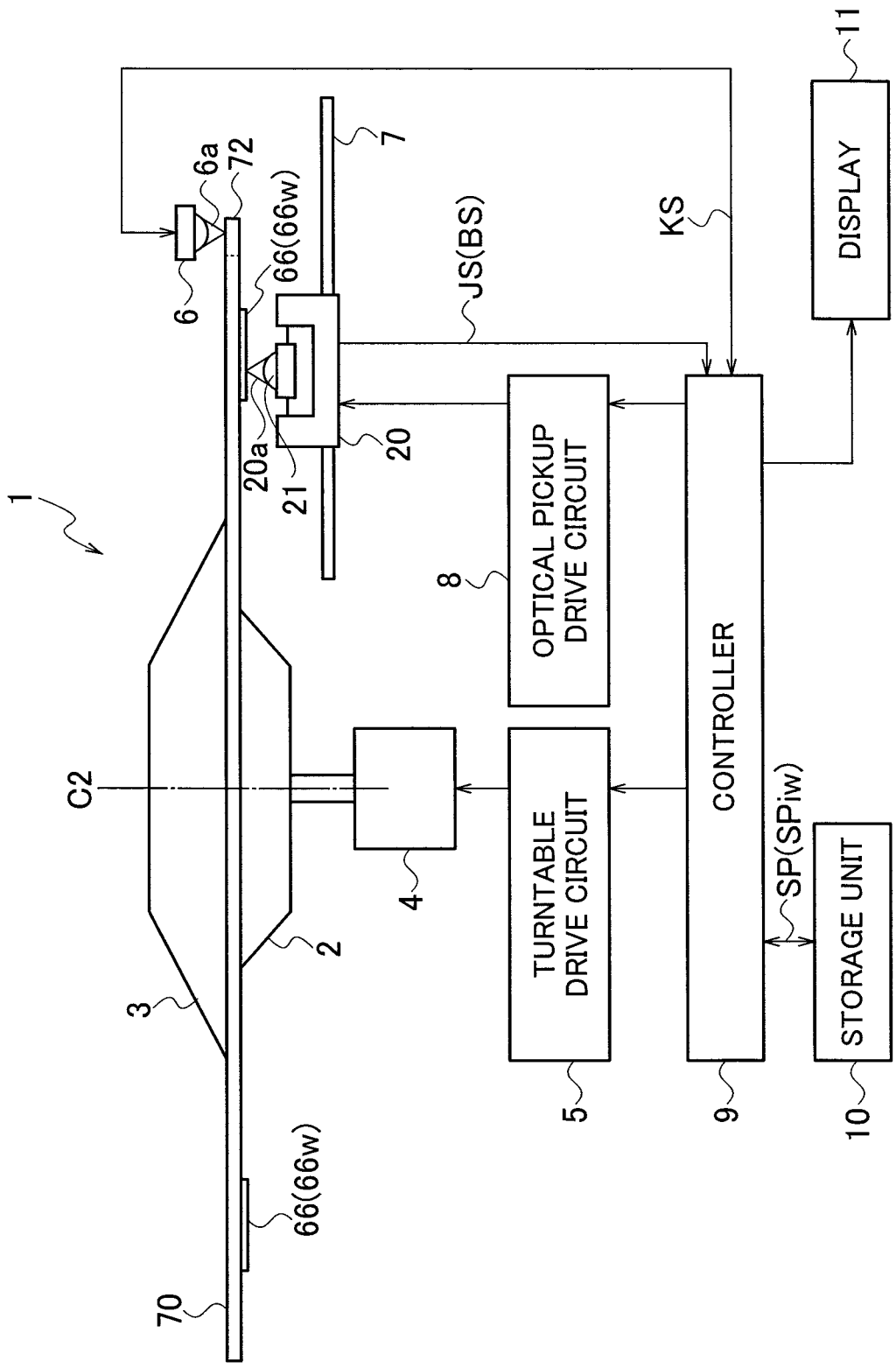
FIG. 6 is a configuration diagram showing an analysis device according to one or more embodiments.

The clamper 3 is driven in directions separating from and approaching the turntable 1, namely, in the upper and lower directions in FIG. 6. The specimen analysis disc 70 is held by the clamper 3 and the turntable 2 when the clamper 3 is driven in the lower direction.

The turntable drive unit 4 drives the turntable 2 to rotate on a rotation axis C2 together with the specimen analysis disc 70 and the clamper 3. A spindle motor may be used as the turntable drive unit 4.

The turntable drive circuit 5 controls the turntable drive unit 4. For example, the turntable drive circuit 5 controls the turntable drive unit 4 such that the turntable 2 rotates at a constant linear velocity together with the specimen analysis disc 70 and the clamper 3.

The reference position detection sensor 6 is placed adjacent to the circumferential edge of the specimen analysis disc 70. The reference position detection sensor 6 is an optical sensor such as a photoreflector, for example.

The reference position detection sensor 6 emits detection light 6a toward the circumferential edge of the rotating specimen analysis disc 70, and receives the reflected light from the specimen analysis disc 70.

The reference position detection sensor 6 detects the slit 72 of the specimen analysis disc 70, generates a reference position detection signal KS, and outputs the signal to the controller 9. The reference position detection signal KS is a pulse signal which rises to be on when the slit 72 reaches the detection position of the reference position detection sensor 6, namely, the position to which the detection light 6a is radiated, and falls to be off when the slit 72 passes through the detection position.

The reference position detection sensor 6 detects the reference position per rotation period and per track of the specimen analysis disc 70. A transmission-type optical sensor may be used as the reference position detection sensor 6. The reference position detection sensor 6 of this type emits the detection light 6a to the specimen analysis disc 70 and receives the detection light 6a passing through the slit 72, so as to detect the reference position per rotation period and per track of the specimen analysis disc 70.

The guide shaft 7 is placed in parallel to the specimen analysis disc 70 in the radial direction of the specimen analysis disc 70.

The optical pickup 20 is supported by the guide shaft 7. The optical pickup 20 is driven along the guide shaft 7 in the direction perpendicular to the rotation axis C2 of the turntable 2, in the radial direction of the specimen analysis disc 70, and in parallel to the specimen analysis disc 70.

The optical pickup 20 includes an objective lens 21. The optical pickup 20 emits laser light 20a to the specimen analysis disc 70. The laser light 20a is condensed by the objective lens 21 on the track regions 75 provided with the reaction regions 66 on the specimen analysis disc 70. The optical pickup 20 is driven in the radial direction of the rotating specimen analysis disc 70 so that the laser light 20a scans the recesses 74 corresponding to the tracks, as shown in FIG. 4.

The optical pickup 20 receives the reflected light from the specimen analysis disc 70. The optical pickup 20 detects a reception level of the reflected light, generates a light reception level signal JS, and outputs the signal to the controller 9.

The optical pickup drive circuit 8 controls the operation of the optical pickup 20. The optical pickup drive circuit 8 moves the optical pickup 20 along the guide shaft 7 or moves the objective lens 21 of the optical pickup 20 in the vertical direction.

The controller 9 controls the turntable drive circuit 5 and the optical pickup drive circuit 8. A central processing unit (CPU) may be used as the controller 9, for example.

The controller 9 controls the turntable drive circuit 5 to stop or rotate the turntable 2 at a constant linear velocity, for example. The controller 9 controls the optical pickup drive circuit 8 to move the optical pickup 20 to a target position in the radial direction of the specimen analysis disc 70 or adjust the position of the objective lens 21 in the vertical direction so as to condense the laser light 20a on the track regions 75.

The controller 9 detects the reference position per rotation period and per track of the specimen analysis disc 70 according to the reference position detection signal KS output from the reference position detection sensor 6. The controller 9 specifies the reaction regions 66 based on the reference position detected.

The storage unit 10 stores measurement parameters SP for every track. The measurement parameters SP include measurement information such as the number of the reaction regions 66, the time corresponding to the distance from the slit 72 as a reference position defining portion to each reaction region 66, and the timing of measurement gate signals GS of each track (refer to FIG. 12).

The controller 9 reads out the measurement parameters SP from the storage unit 10, and sequentially generates the measurement gate signals GS for each reaction region 66 according to the measurement parameters SP. The controller 9 extracts a nanoparticle pulse signal BS per measurement gate signal GS from the light reception level signal JS output from the optical pickup 20.

The controller 9 counts the number of the nanoparticles labeling the detection target substances 63 from the extracted nanoparticle pulse signal BS. The controller adds up the number of the nanoparticles 64 of the respective tracks in each reaction region 66 to store the number in the storage unit 10. The controller 9 adds up the number of the nanoparticles 64 of the respective reaction regions 66 and displays the sum on the display unit 11. The number of the nanoparticles 64 displayed corresponds to the number of the detection target substances 63.

[Analysis Method]

An analysis method of analyzing the detection target substances 63, more particularly, a method of analyzing the nanoparticles 64 labeling the detection target substances 63 by the analysis device 1, is described below with reference to FIG. 7 to FIG. 13.

Figure 7:
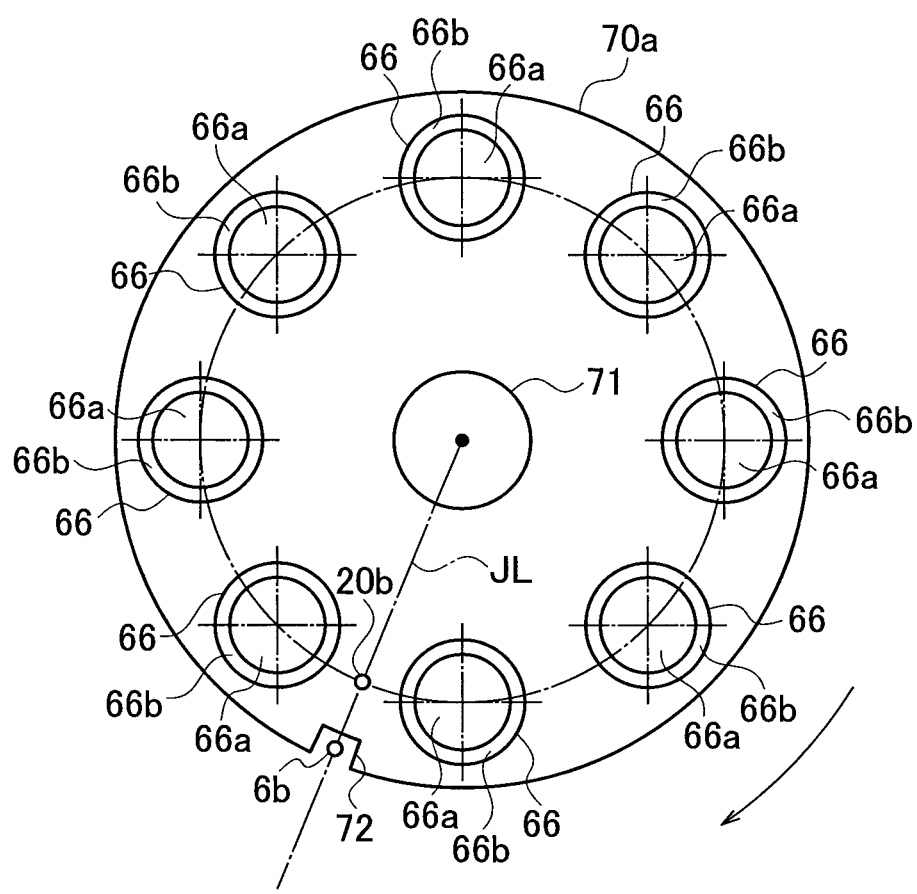
FIG. 7 is a plan view illustrating a positional relationship between detection positions of a reference position detection sensor and an optical pickup, and positions of a slit and reaction regions on the specimen analysis disc.

FIG. 7 schematically illustrates a positional relationship between the detection positions of the reference position detection sensor 6 and the optical pickup 20, and the positions of the slit 72 and the respective reaction regions 66 in the specimen analysis disc 70. Reference sign 6*b* in FIG. 7 indicates the detection position of the reference position detection sensor 6. The axial line JL corresponds to the guide shaft 7. The optical pickup 20 moves along the axial line JL in the radial direction of the specimen analysis disc 70. Reference sign 20*b* in FIG. 7 indicates the detection position of the optical pickup 20.

FIG. 7 illustrates the specimen analysis disc 70*a* in which the reaction regions 66 are formed at predetermined positions. The reaction regions 66 are arranged at regular intervals such that the respective center points are located on the common circle concentric with the specimen analysis disc 70*a*. The reaction regions 66 are thus located at the predetermined and preferred positions on the specimen analysis disc 70*a*.

FIG. 7 illustrates the state in which the detection position 20*b* of the optical pickup 20 is located on the same circle on which the center points of the reaction regions 66 are located. The detection position 6*b* of the reference position detection sensor 6 is located on the axial line JL in FIG. 7, but is not limited to this illustration. The detection position 6*b* may be any position at which the slit 72 can be detected at the circumferential edge of the specimen analysis disc 70*a*.

During the process of forming the reaction regions 66, the solutions such as the sample solution and the buffer solution are injected into the wells 61 and then incubated. The solutions injected tend to remain at peripheries of the bottoms of the wells 61. Impurities in the remaining solutions may be kept as residues at the peripheries of the bottoms of the wells 61.

The peripheries of the reaction regions 66 correspond to the peripheries of the bottoms of the wells 61. Detecting the peripheries of the reaction regions 66 at which impurities tend to remain as residues may lead to a decrease in accuracy of the analysis. In order to deal with this problem, the area of each reaction region 66 excluding the periphery is defined as an analysis-target reaction region 66*a* which is a target to be analyzed, while the periphery of each reaction region 66 is defined as an analysis-ineligible reaction region 66*b* which is excluded from the target to be analyzed. The nanoparticles 64 captured only in the analysis-target reaction regions 66*a* are analyzed, so as to improve the accuracy of the analysis.

Figure 8:
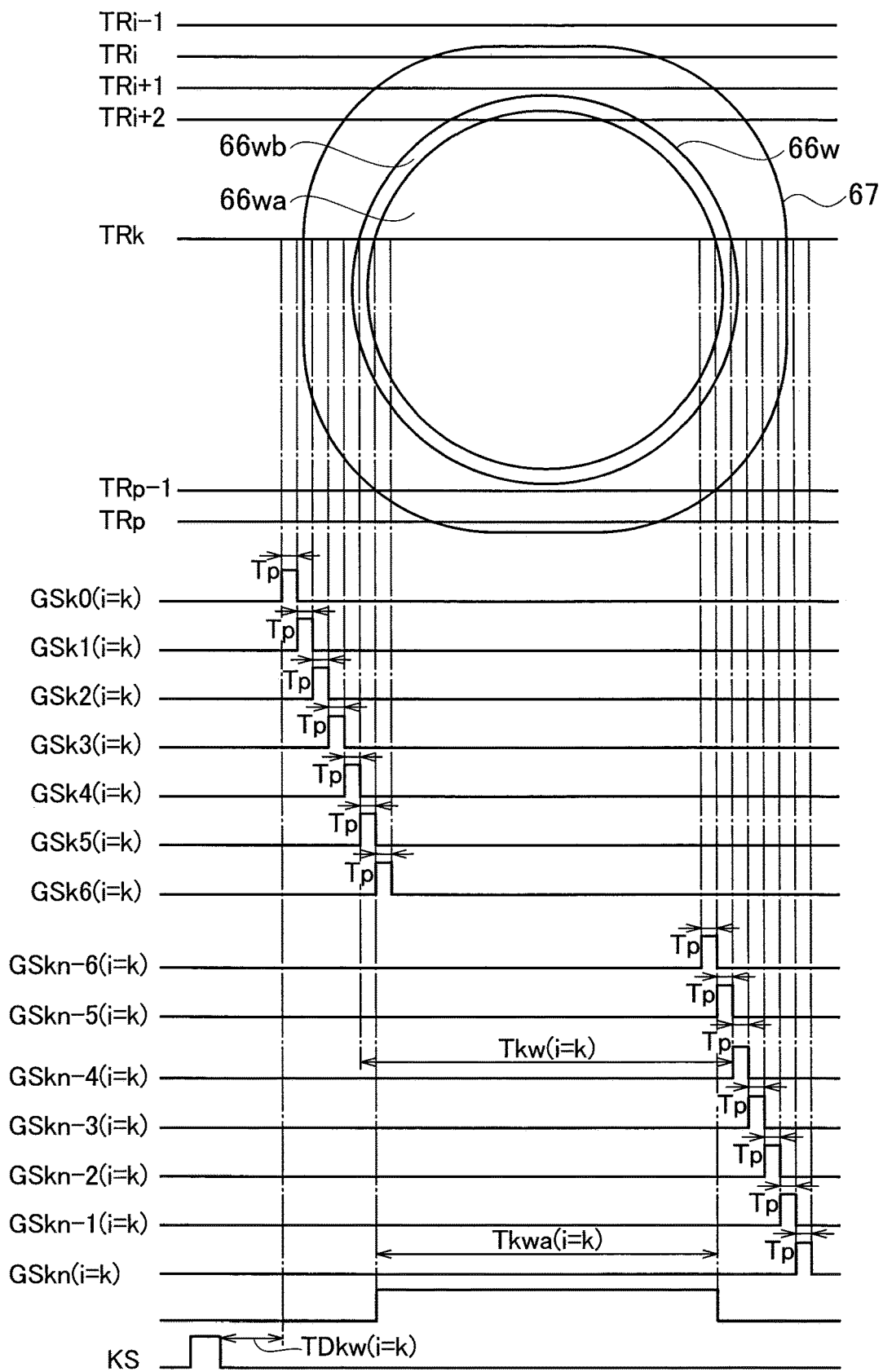
FIG. 8 is a time chart showing a relationship between a reaction region formed at a predetermined position and measurement gate signals.

A relationship between the reaction region 66 formed at a predetermined position and the measurement gate signals GS is described below with reference to the time chart shown in FIG. 8. FIG. 8 illustrates the reaction region 66 formed at a predetermined position (a preferred position). Reference sign 67 indicates a tolerance region. The tolerance region 67 will be described below.

Figure 9:
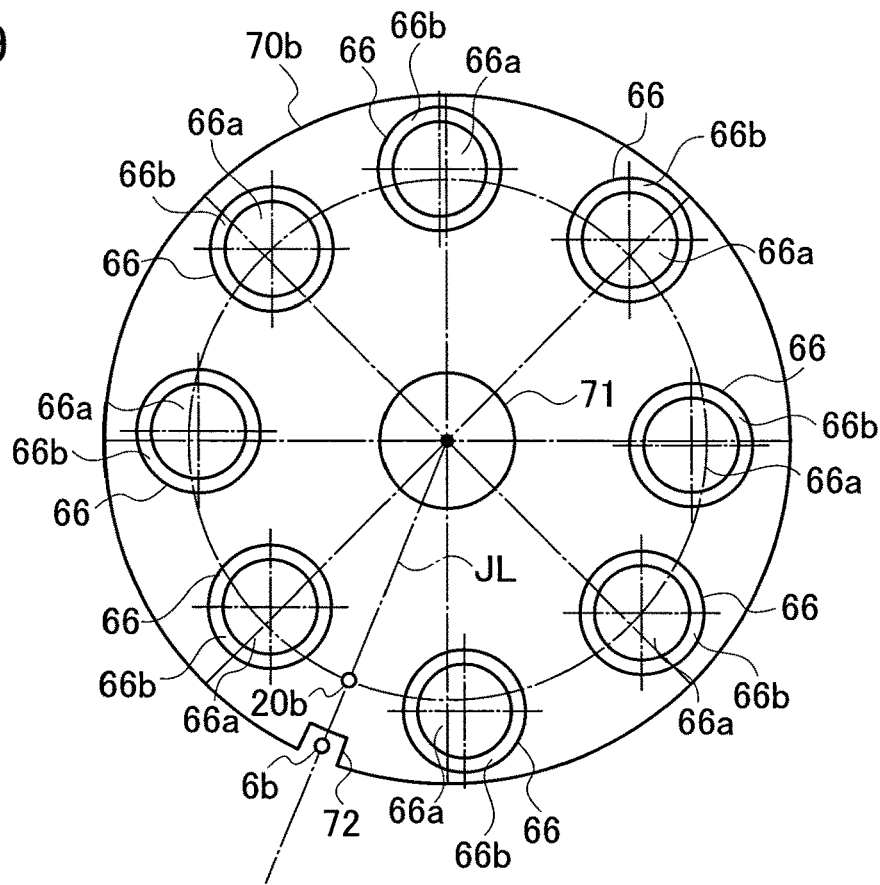
FIG. 9 is a plan view showing a specimen analysis disc in which reaction regions are displaced from predetermined positions.

The reaction regions 66 may be formed at positions displaced from the predetermined positions on the specimen analysis disc 70 because of a tolerance in positioning between the cartridge 80 and the specimen analysis disc 70 or displacement of the cartridge 80 on the specimen analysis disc 70 caused by deformation of the seal member 90. FIG. 9 illustrates the specimen analysis disc 70*b* in which the reaction regions 66 are displaced from the predetermined positions. The direction or degree of displacement of the reaction regions 66 may vary depending on the reaction regions 66.

The tolerance region 67 is determined while taking account of a case in which the reaction regions 66 are displaced from the predetermined positions. The respective reaction regions 66 may be formed at any position within the tolerance region 67.

A specific method of analyzing the nanoparticles 64 is described below with reference to the flow charts shown in FIG. 10A, FIG. 10B, and FIG. 10C.

Figure 10A:
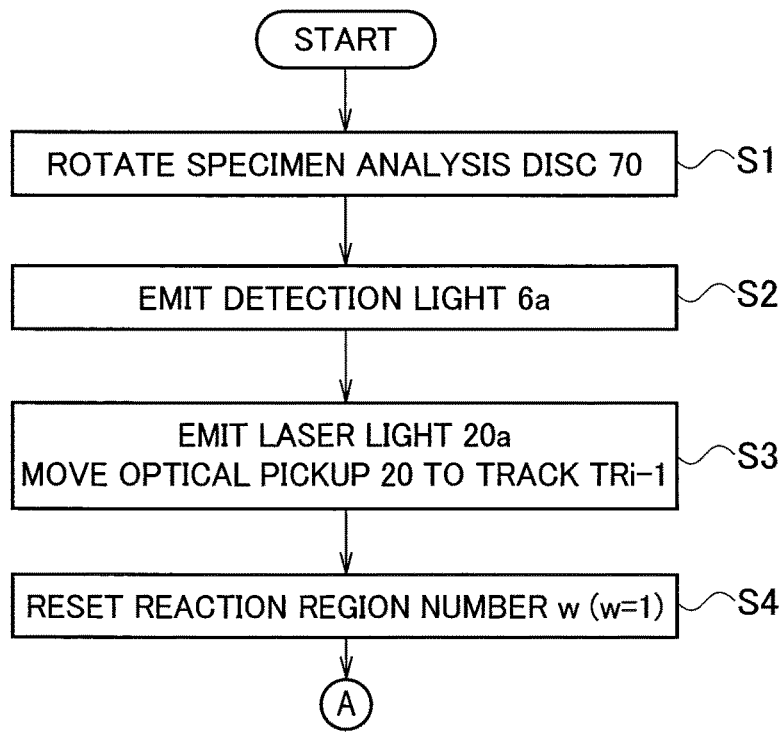
FIG. 10A is a flow chart for describing a method of analyzing the nanoparticles by the analysis device according to one or more embodiments.

In step S1 in FIG. 10A, the controller 9 controls the turntable drive circuit 5 to direct the turntable drive unit 4 to turn the turntable 2, so that the specimen analysis disc 70 rotates at a constant linear velocity.

In step S2, the controller 9 directs the reference position detection sensor 6 to emit the detection light 6*a* to the specimen analysis disc 70.

In step S3, the controller 9 directs the optical pickup 20 to emit the laser light 20*a* to the specimen analysis disc 70. The controller 9 controls the optical pickup drive circuit 8 to move the optical pickup 20 to a track TRi−1 on the outside of the tolerance region 67. As shown in FIG. 8, the tolerance region 67 is defined across a plurality of tracks TRi to TRp. The track TRi−1 is located immediately in front of the track TRi on one side of the tolerance region 67 (on the upper side in FIG. 9). The track TRp is located on the other side in the tolerance region 67. The final indications "i" to "p" for the tracks TRi to TRp and the final indication "i−1" for the track TRi−1 each correspond to the track number.

Step S3 is not necessarily performed after step S2. Step S2 may be performed after step S3, or step S2 and step S3 may be performed simultaneously.

In step S4, the controller 9 resets the reaction region number w (w=1). For example, the reaction region number w=1 denotes the reaction region 66 detected first on the basis of the slit 72 serving as a reference position. The reaction region number w=m denotes the reaction region 66 detected last on the basis of the slit 72. In one or more embodiments, the number of the reaction regions 66 is eight, and the reaction region number w=m is thus eight (m=8).

Figure 10B:
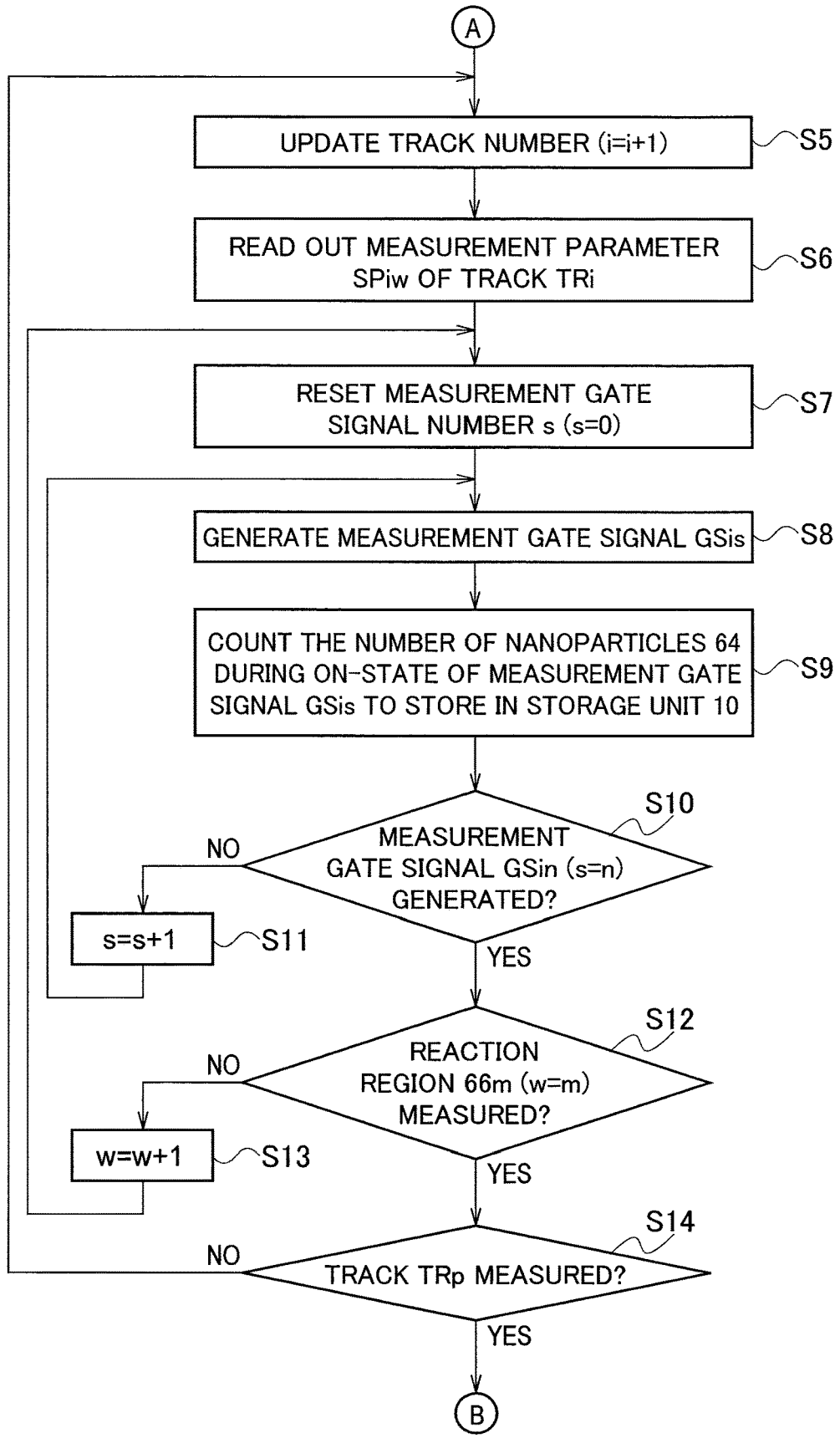
FIG. 10B is a flow chart for describing the method of analyzing the nanoparticles by the analysis device according to one or more embodiments.

In step S5 in FIG. 10B, the controller 9 directs the reference position detection sensor 6 to detect a fall of the reference position detection signal KS generated by the detection of the slit 72, so as to update the track number (i=i+1). The controller 9 controls the optical pickup drive circuit 8 to move the optical pickup 20 from the track TRi−1 to the next track TRi. As a result, the tolerance region 67 passes through the detection position of the optical pickup 20.

In step S6, the controller 9 reads out the measurement parameter SPiw of the track TRi from the storage unit 10. The measurement parameter SPiw is a measurement parameter of the track TRi in the reaction region 66*w* (w=1 to m).

The measurement parameter SPiw includes measurement information such as the time TDiw from the fall of the reference position detection signal KS to the rise of the first measurement gate signal GSi0 (s=0), and the time for generating each measurement gate signal GSis. The final indication "s" for the measurement gate signal GSis is a variable and denotes the measurement gate signal number. The time TDiw is determined per track in accordance with the positional relationship between the slit 72 and the tolerance region 67w, and the velocity of rotation of the specimen analysis disc 70.

In step S7, the controller 9 resets the measurement gate signal number s (s=0), according to the measurement parameter SPiw, at the point when the time TDiw has passed since the fall of the reference position detection signal KS is detected.

In step S8, the controller 9 generates the measurement gate signal GSis having a pulse width Tp according to the measurement parameter SPiw so that the signal rises at the point when the time TDiw has passed since the fall of the reference position detection signal KS is detected. The pulse width Tp is determined depending on the analysis accuracy required for the analysis device 1. A decrease in the pulse width Tp improves the measurement position accuracy.

In step S9, the controller 9 detects the nanoparticle pulse signal BS from the light reception level signal JS output from the optical pickup 20 during the period in which the measurement gate signal GSis is in the ON state (which corresponds to the pulse width Tp), so as to count the number of the nanoparticles 64. The light reception level signal JS may include noise other than the nanoparticle pulse signal BS. The controller 9 thus compares the pulse signal included in the light reception level signal JS with a threshold Vp so as to define the pulse signal less than or equal to the threshold Vp as the nanoparticle pulse signal BS. The controller 9 stores the number of the measured nanoparticles 64 in association with the track number and the reaction region number w.

In step S10, the controller 9 determines whether the measurement gate signal GSin (s=n) is generated. The measurement gate signal GSin is a signal generated last in the track TRi. The measurement gate signal GSin is determined according to the measurement parameter SPiw read out from the storage unit 10.

When the measurement gate signal GSin is determined not to be generated yet (NO) in step S10, the controller 9 updates the measurement gate signal number (s=s+1) in step S11, and generates the next measurement gate signal GSis+1 in step S8. The measurement gate signal GSis+1 is generated such that the time of the rise of the measurement gate signal GSis+1 conforms to the time of the fall of the measurement gate signal GSis.

When the measurement gate signal GSin is determined to be generated (YES) in step S10, the controller 9 then determines whether the reaction region 66m (w=m) is measured in step S12.

When the reaction region 66m is determined not to be measured yet (NO) in step S12, the controller 9 updates the reaction region number (w=w+1) in step S13, and resets the measurement gate signal number s (s=0) in step S7 at the point when the time TDiw+1 has passed since the fall of the reference position detection signal KS is detected.

When the reaction region 66m is determined to be measured (YES) in step S12, the controller 9 then determines whether the track TRp which is the last track within the tolerance region 67 is measured in step S14.

When the track TRp is determined not to be measured yet (NO) in step S14, the controller 9 directs the reference position detection sensor 6 to detect the fall of the reference position detection signal KS generated by the detection of the slit 72, so as to update the track number (i=i+1) in step S5. The controller 9 controls the optical pickup drive circuit 8 to move the optical pickup 20 from the track TRi to the next track TRi+1.

Figure 10C:
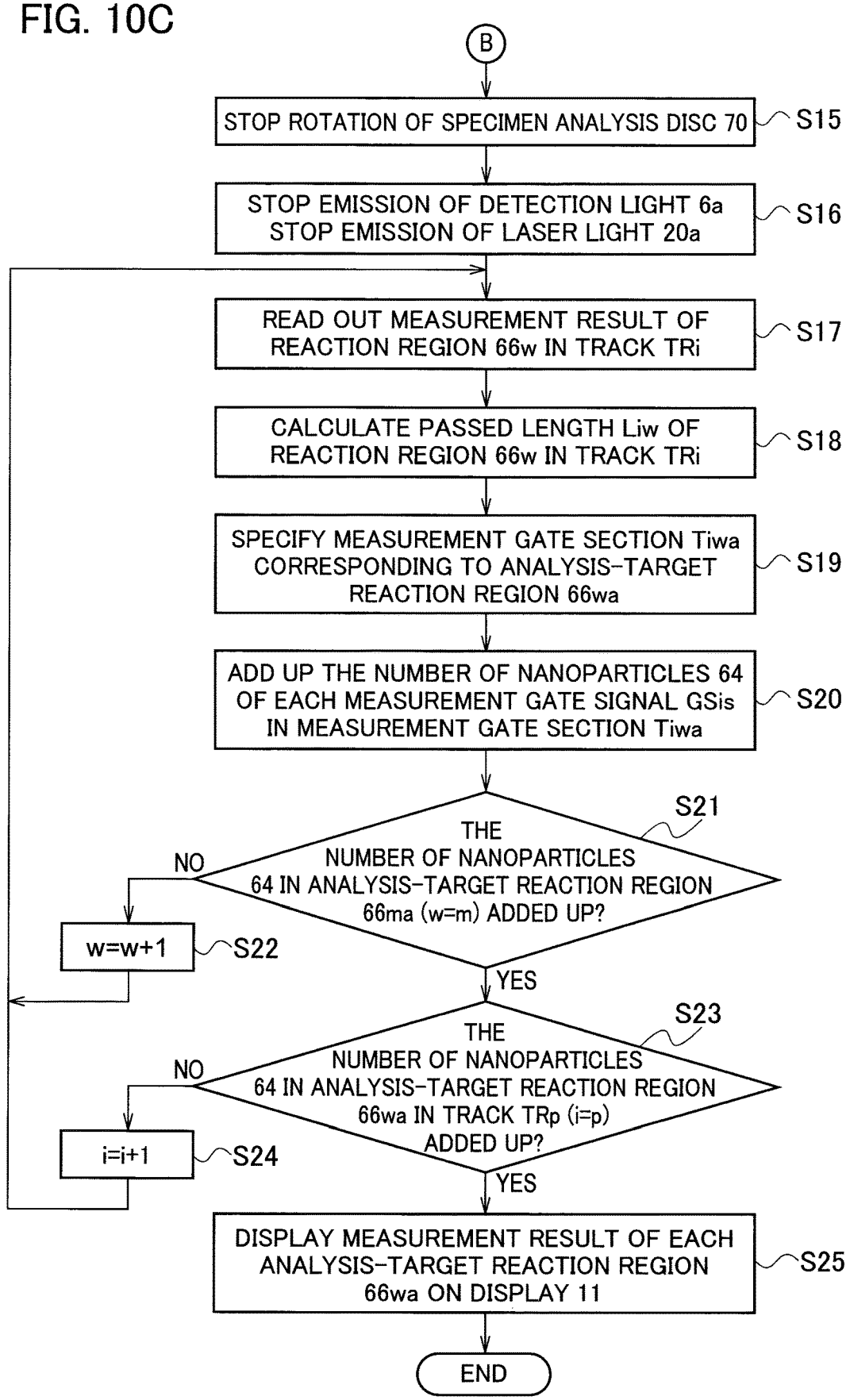
FIG. 10C is a flow chart for describing the method of analyzing the nanoparticles by the analysis device according to one or more embodiments.

When the track TRp is determined to be measured (YES) in step S14, the controller 9 controls the turntable drive circuit 5 to stop the rotation of the specimen analysis disc 70 in step S15 in FIG. 10C.

In step S16, the controller 9 controls the reference position detection sensor 6 and the optical pickup 20 to stop the emission of the detection light 6a and the laser light 20a. In step S17, the controller 9 reads out, from the storage unit 10, the measurement result of the reaction region 66w obtained by the respective measurement gate signals GSis in the track TRi.

In step S18, the controller 9 calculates a passed length Liw of the reaction region 66w in the track TRi according to the measurement result obtained by the respective measurement gate signals GSis. In step S19, the controller 9 refers to a table list preliminarily stored in the storage unit 10 to specify a measurement gate section Tiwa corresponding to the analysis-target reaction region 66wa based on the passed length Liw.

In step S20, the controller 9 adds up the number of the nanoparticles 64 of the respective measurement gate signals GSis in the measurement gate section Tiwa of the analysis-target reaction region 66wa. The controller 9 adds the sum of the nanoparticles 64 to the measurement result Rw to store the number in the storage unit 10.

In step S21, the controller 9 determines whether the number of the nanoparticles 64 of the respective measurement gate signals GSis in the measurement gate section Tiwa of the analysis-target reaction region 66ma (w=m) is added up, the sum of the nanoparticles 64 is added to the measurement result Rm (w=m), and the added number is stored in the storage unit 10.

When it is determined to be NO in step S21, the controller 9 updates the reaction region number (w=w+1) in step S22, and reads out, from the storage unit 10, the measurement result obtained by the respective measurement gate signals GSis in the track TRi in the reaction region 66w+1 in step S17.

When it is determined to be YES in step S21, the controller 9 determines whether the number of the nanoparticles 64 in the track TRp (i=p) in the measurement gate section Tiwa of the analysis-target reaction region 66wa is added to the measurement result Rw, and the added number is stored in the storage unit 10 in step S23.

When it is determined to be NO in step S23, the controller 9 updates the track number (i=i+1) in step S24, and reads out, from the storage unit 10, the measurement result obtained by the respective measurement gate signals GSis in the track TRi+1 in the reaction region 66w in step S17.

When it is determined to be YES in step S23, the controller 9 directs the display unit 11 to display the measurement results of the respective analysis-target reaction regions 66wa in step S25.

[Method of Specifying Analysis-Target Reaction Region]

A method of specifying analysis-target reaction regions 66wa is described below with reference to FIG. 8 and FIG. 11 to FIG. 13.

Figure 11:
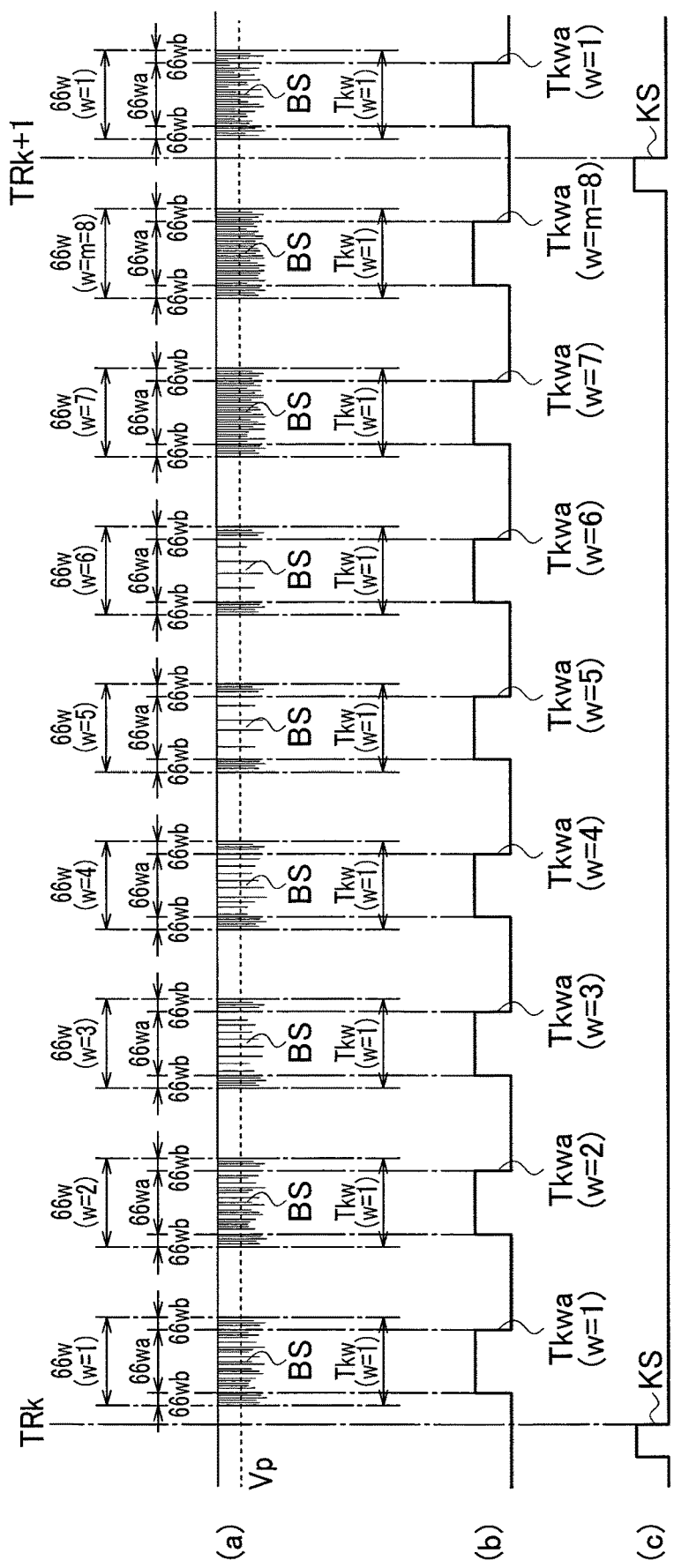
FIG. 11 is a time chart showing a relationship among nanoparticle pulse signal groups, measurement gate sections, and reference position detection signals KS in the reaction regions formed at the predetermined positions.

FIG. 8 and FIG. 11 illustrate the case in which the reaction regions 66w are formed at the predetermined positions.

As shown in FIG. 8, in the track TRk (i=k (i<k<p), the measurement gate signal GSk0 (s=0) with the pulse width Tp is generated so as to rise at the point when the time TDkw has passed since the fall of the reference position detection signal KS is detected. The following measurement gate signals GSk1 (s=1) to GSkn (s=n) with the pulse width Tp are then generated sequentially.

During the period in which the measurement gate signals GSk0 to GSk4 are in the ON state, no nanoparticle pulse signal BS is detected, since the reaction region 66w does not reach the detection position of the optical pickup 20 yet.

During the period Tkw (i=k) in which the measurement gate signals GSk5 to GSkn−5 are in the ON state, the reaction region 66w passes through the detection position of the optical pickup 20, so that the nanoparticle gate signals BS are detected. The nanoparticle gate signals BS detected when the measurement gate signals GSk5 and GSkn−5 are each in the ON state are nanoparticle gate signals detected in the analysis-ineligible reaction region 66wb.

The controller 9 multiplies the period Tkw by the velocity of rotation of the specimen analysis disc 70 in the track TRk, so as to calculate the passed length Lkw (i=k) of the reaction region 66w. The controller 9 refers to the table list stored in the storage unit 10 to read out the passed length Lkwa (i=k) of the analysis-target reaction region 66wa based on the passed length Lkw of the reaction region 66w in the track TRk (i=k), so as to specify the measurement gate section Tkwa (i=k) corresponding to the passed length Lkwa. In the track TRk, the period in which the measurement gate signals GSk6 to GSkn−6 are in the ON state is defined as the measurement gate section Tkwa.

(a) of FIG. 11 illustrates groups of the nanoparticle signals BS in the track TRk (i=k) detected in the specimen analysis disc 70a in which the reaction regions 66w are located at the predetermined positions (refer to FIG. 7). (b) of FIG. 11 illustrates the measurement gate sections Tkwa. (c) of FIG. 11 illustrates the reference position detection signals KS.

The analysis device and the analysis method according to one or more embodiments calculate the passed length Liw of each reaction region 66w in the track TRi to specify the measurement gate section Tiwa. Since the nanoparticles 64 are measured only in the analysis-target reaction region 66wa, the analysis device and the analysis method can improve the analysis accuracy as compared with the case in which the nanoparticles 64 are measured in the entire reaction region 66w.

Figure 12:
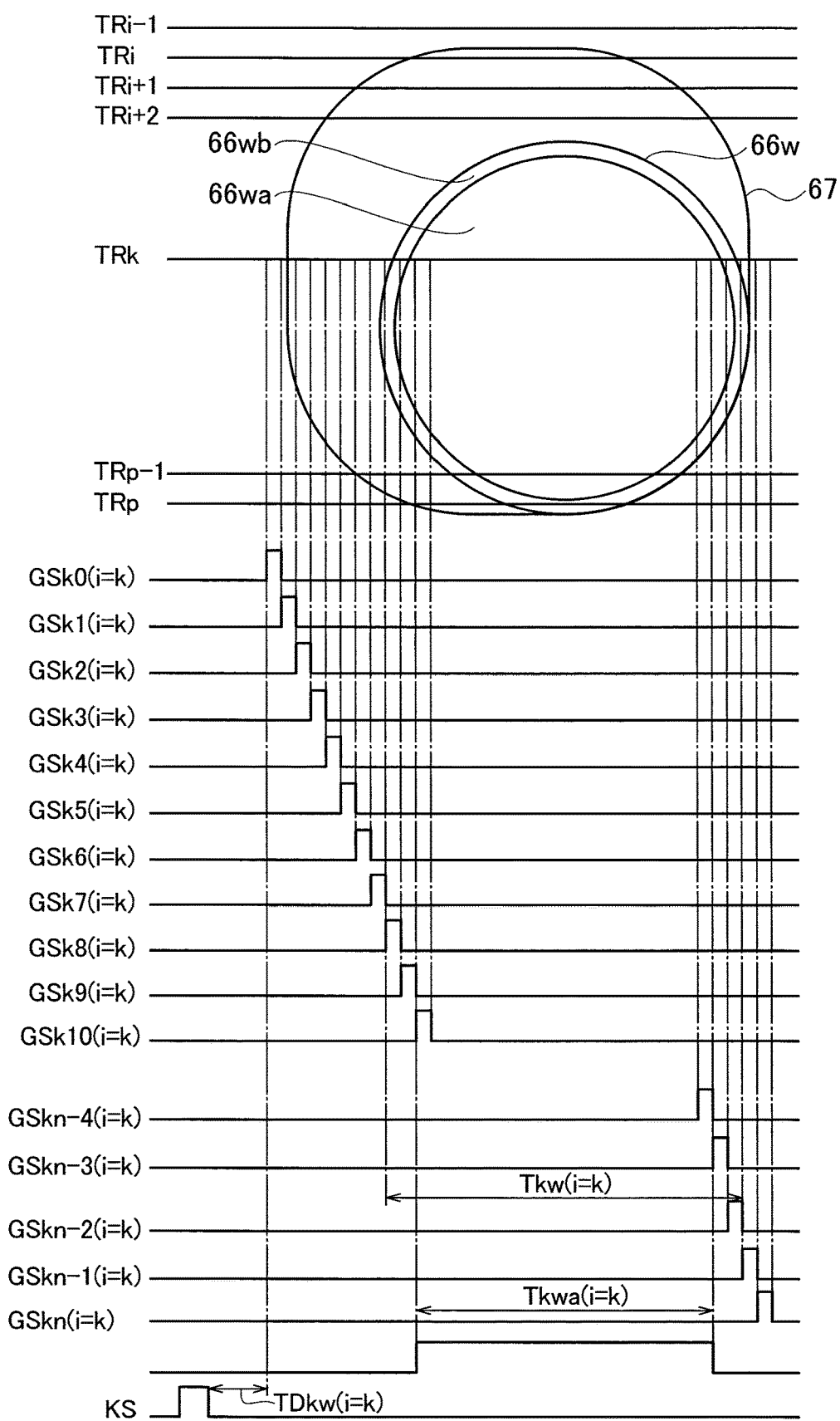
FIG. 12 is a time chart showing a relationship between a reaction region displaced from a predetermined position and measurement gate signals.
Figure 13:
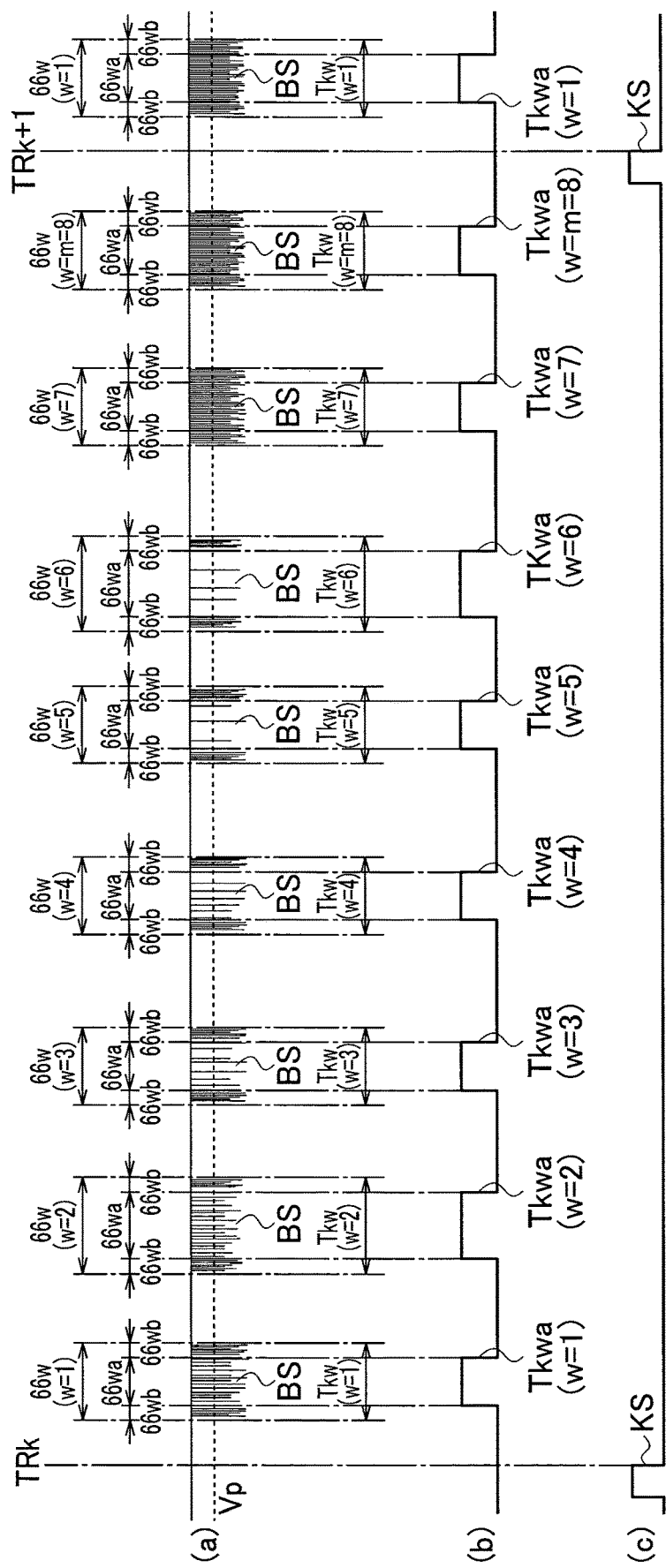
FIG. 13 is a time chart showing a relationship among nanoparticle pulse signal groups, measurement gate sections, and reference position detection signals KS in the reaction regions displaced from the predetermined positions.

FIG. 12 and FIG. 13 illustrate the case in which the reaction regions 66w are displaced from the predetermined positions.

In the track TRk, the measurement gate signal GSk0 (s=0) with the pulse width Tp is generated so as to rise at the point when the time TDkw has passed since the fall of the reference position detection signal KS is detected. The following measurement gate signals GSk1 (s=1) to GSkn (s=n) with the pulse width Tp are then generated sequentially.

During the period in which the measurement gate signals GSk0 to GSk7 are in the ON state, no nanoparticle pulse signal BS is detected, since the reaction region 66w does not reach the detection position of the optical pickup 20 yet.

During the period Tkw (i=k) in which the measurement gate signals GSk8 to GSkn−2 are in the ON state, the reaction region 66w passes through the detection position of the optical pickup 20, so that the nanoparticle gate signals BS are detected. The nanoparticle gate signals BS detected when the measurement gate signals GSk8, GSk9, GSkn−3, and GSkn−2 are each in the ON state include nanoparticle gate signals detected in the analysis-ineligible reaction region 66wb.

The controller 9 multiplies the period Tkw by the velocity of rotation of the specimen analysis disc 70 in the track TRk, so as to calculate the passed length Lkw (i=k) of the reaction region 66w. The controller 9 refers to the table list stored in the storage unit 10 to read out the passed length Lkwa (i=k) of the analysis-target reaction region 66wa based on the passed length Lkw of the reaction region 66w in the track TRk (i=k), so as to specify the measurement gate section Tkwa (i=k) corresponding to the passed length Lkwa. In the track TRk, the period in which the measurement gate signals GSk10 to GSkn−4 are in the ON state is defined as the measurement gate section Tkwa.

(a) of FIG. 13 illustrates groups of the nanoparticle signals BS in the track TRk (i=k) detected in the specimen analysis disc 70b in which the reaction regions 66w are displaced from the predetermined positions (refer to FIG. 9). (b) of FIG. 13 illustrates the measurement gate sections Tkwa. (c) of FIG. 13 illustrates the reference position detection signals KS.

The analysis device and the analysis method according to one or more embodiments calculate the passed length Liw of each reaction region 66w in the track TRi to specify the measurement gate section Tiwa. Accordingly, the nanoparticles 64 are measured only in the analysis-target reaction region 66wa also in the case in which the reaction regions 66w are displaced from the predetermined positions.

The analysis device and the analysis method according to one or more embodiments thus can also accurately detect the nanoparticles 64 on the specimen analysis disc 70b in which the reaction regions 66w are displaced from the predetermined positions.

It should be understood that the present invention is not intended to be limited to one or more embodiments described above, and various modifications will be apparent to those skilled in the art without departing from the scope of the present invention.

While the analysis device 1 according to one or more embodiments is illustrated with the specimen analysis disc 70 installed on the turntable 2 such that the reaction regions 66 face down, the present invention is not limited to this configuration. The specimen analysis disc 70 may be installed with the reaction regions 66 facing up.

What is claimed is:

1. An analysis device comprising:
    a turntable holding a specimen analysis disc having a reaction region on which nanoparticles binding to substances to be detected are captured;
    a turntable drive unit configured to rotate the turntable;
    a turntable drive circuit configured to control the turntable drive unit;
    an optical pickup driven in a direction perpendicular to a rotation axis of the turntable, and configured to emit laser light to the reaction region, to receive a reflected light from the reaction region, to detect a reception level of the reflected light and to generate a light reception level signal as an electrical signal based on the detected reception level of the reflected light;
    an optical pickup drive circuit configured to control an operation of the optical pickup; and
    a controller configured to control the turntable drive circuit and the optical pickup drive circuit,
    wherein the controller sequentially generates a plurality of measurement gate signals for counting a number of the nanoparticles captured on the reaction region, each of the measurement gate signals being an electrical pulse signal for receiving the light reception level signal, counts the number of the nanoparticles of each of the measurement gate signals based on the light reception level signal, specifies a measurement gate section indicating a measurement timing and a measurement time length corresponding to the reaction region according to the counted number of the nanoparticles per measurement gate signal, and adds up the number of the nanoparticles of the respective measurement gate signals in the measurement gate section.

2. The analysis device according to claim 1, further comprising a storage unit storing a measurement parameter for generating the measurement gate signals and a table list for specifying the measurement gate section, wherein the controller reads out the measurement parameter from the storage unit to sequentially generate the plurality of measurement gate signals, and specifies the measurement gate section by referring to the table list.

3. The analysis device according to claim 1, wherein:
the specimen analysis disc includes a reference position defining portion for defining a reference position;
the analysis device further comprises a reference position detection sensor configured to detect the reference position defining portion to generate a reference position detection signal; and
the controller specifies the reaction region based on the reference position detection signal.

4. An analysis method comprising:
rotating a specimen analysis disc having a reaction region on which nanoparticles binding to substances to be detected are captured and emitting laser light to the reaction region;
receiving a reflected light from the reaction region;
detect a reception level of the reflected light;
generating a light reception level signal that is an electrical signal based on the detected reception level of the reflected light;
sequentially generating a plurality of measurement gate signals for counting a number of the nanoparticles captured on the reaction region, each of the measurement gate signals being an electrical puke signal for receiving the light reception level signal;
counting the number of the nanoparticles of each of the measurement gate signals based on the light reception level signal;
specifying a measurement gate section indicating a measurement timing and a measurement time length corresponding to the reaction region according to the counted number of the nanoparticles per measurement gate signal; and
adding up the number of the nanoparticles of the respective measurement gate signals in the measurement gate section.

* * * * *